US012616368B2

(12) United States Patent
Engebretsen et al.

(10) Patent No.: US 12,616,368 B2
(45) Date of Patent: May 5, 2026

(54) BEAT RECLASSIFICATION

(71) Applicant: Preventice Solutions, Inc., Rochester, MN (US)

(72) Inventors: David Robert Engebretsen, Cannon Falls, MN (US); Jake Matras, Eagan, MN (US); Timothy Patrick McClanahan, Rochester, MN (US); Benjamin Adam Teplitzky, Lakeville, MN (US); Michael Thomas Edward McRoberts, Mazeppa, MN (US)

(73) Assignee: Preventice Solutions, Inc., Rochester, MN (US)

( * ) Notice: Subject to any disclaimer, the term of this patent is extended or adjusted under 35 U.S.C. 154(b) by 357 days.

(21) Appl. No.: 18/139,714

(22) Filed: Apr. 26, 2023

(65) Prior Publication Data

US 2024/0057864 A1      Feb. 22, 2024

Related U.S. Application Data

(60) Provisional application No. 63/335,621, filed on Apr. 27, 2022.

(51) Int. Cl.
| | |
|---|---|
| *A61B 5/00* | (2006.01) |
| *A61B 5/318* | (2021.01) |
| *A61B 5/339* | (2021.01) |
| *A61B 5/349* | (2021.01) |

(52) U.S. Cl.
CPC .......... *A61B 5/0006* (2013.01); *A61B 5/0022* (2013.01); *A61B 5/318* (2021.01); *A61B 5/339* (2021.01); *A61B 5/349* (2021.01); *A61B 5/7475* (2013.01)

(58) Field of Classification Search
CPC ..... A61B 5/0006; A61B 5/0022; A61B 5/318; A61B 5/339; A61B 5/349; A61B 5/7475; A61B 5/0245; G16H 50/20
See application file for complete search history.

(56) References Cited

U.S. PATENT DOCUMENTS

| | | | | |
|---|---|---|---|---|
| 2021/0338138 | A1* | 11/2021 | Pedalty | A61B 5/33 |
| 2022/0095982 | A1* | 3/2022 | de Saint Victor | A61B 5/339 |
| 2022/0218259 | A1* | 7/2022 | Laversin | G06F 21/6245 |

FOREIGN PATENT DOCUMENTS

EP            3698707 B1 *  6/2023  ............. A61B 5/318

* cited by examiner

*Primary Examiner* — Sana Sahand
(74) *Attorney, Agent, or Firm* — Faegre Drinker Biddle & Reath LLP

(57) ABSTRACT

A method includes receiving, by a first computing system, electrocardiogram (ECG) data and metadata associated with the ECG data. The metadata includes an initial cardiac event classification and an initial beat classification for beats occurring during a first event associated with the initial cardiac event classification. The method further includes displaying the ECG data in a user interface, receiving a command to change the initial cardiac event classification to a subsequent cardiac event classification, and automatically modifying the initial beat classifications to subsequent beat classifications based on the subsequent cardiac event classification.

18 Claims, 8 Drawing Sheets

300

302 — Receive ECG data and metadata, including an initial cardiac event classification and initial beat classifications 304 — Receive a command to change the initial cardiac event classification to a subsequent cardiac event classification 306 — Automatically modify the initial beat classifications to subsequent beat classifications based on the subsequent cardiac event classification

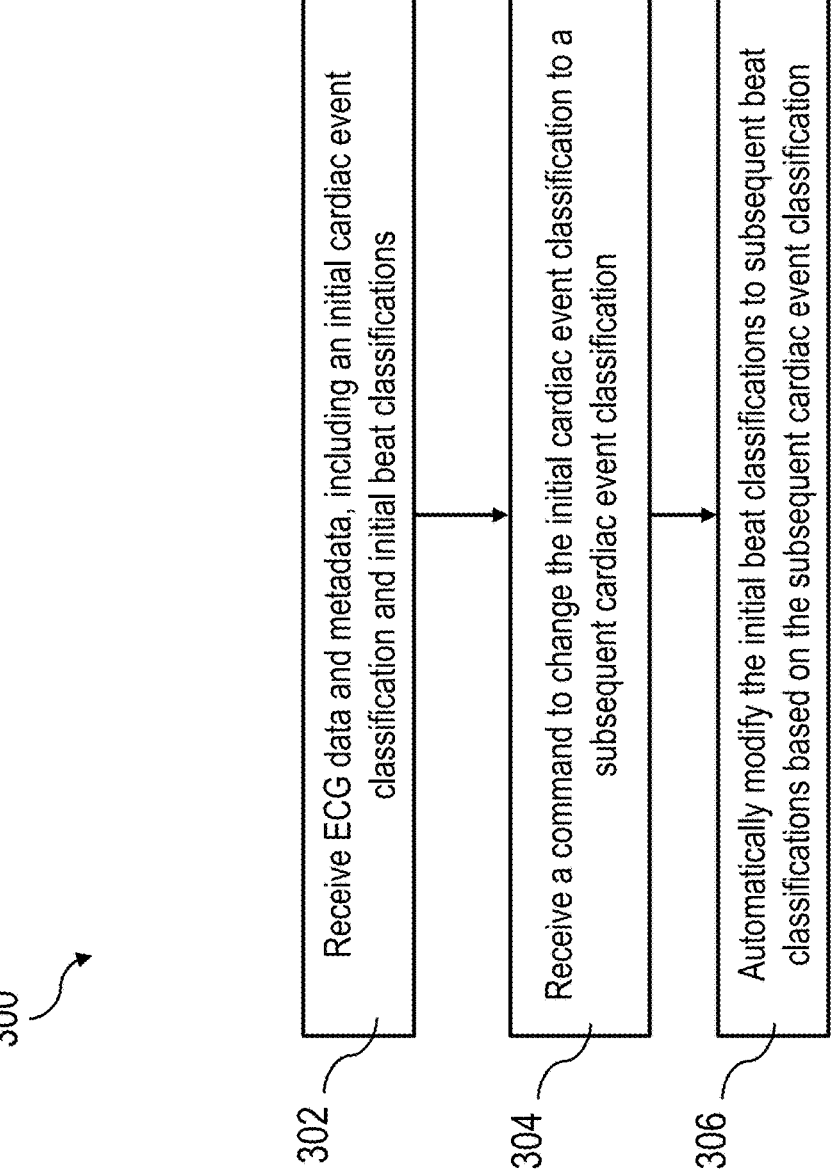

302  Receive ECG data and metadata, including an initial cardiac event classification and initial beat classifications 304  Receive a command to change the initial cardiac event classification to a subsequent cardiac event classification 306  Automatically modify the initial beat classifications to subsequent beat classifications based on the subsequent cardiac event classification

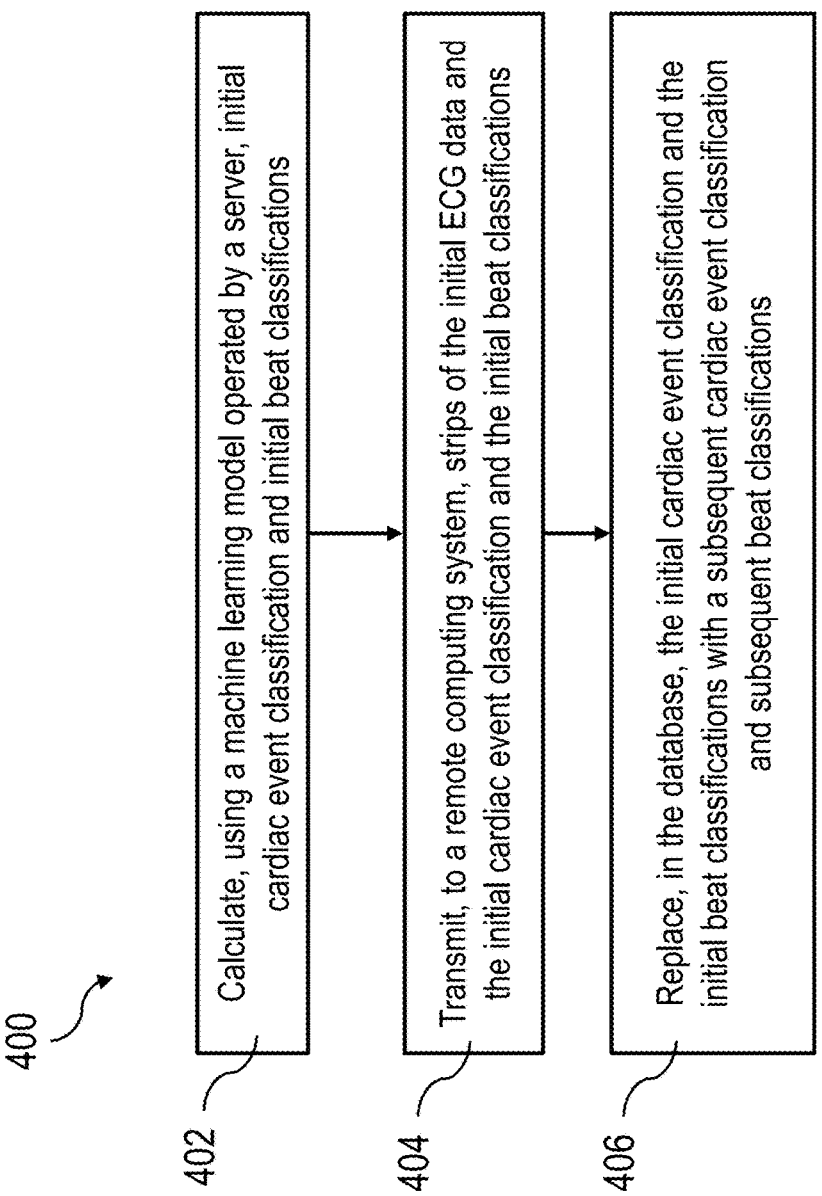

402 — Calculate, using a machine learning model operated by a server, initial cardiac event classification and initial beat classifications 404 — Transmit, to a remote computing system, strips of the initial ECG data and the initial cardiac event classification and the initial beat classifications 406 — Replace, in the database, the initial cardiac event classification and the initial beat classifications with a subsequent cardiac event classification and subsequent beat classifications

BEAT RECLASSIFICATION

CROSS REFERENCE TO RELATED APPLICATION

This application claims priority to Provisional Application No. 63/335,621, filed Apr. 27, 2022, all of which are herein incorporated by reference in their entirety.

TECHNICAL FIELD

The present disclosure relates to devices, methods, and systems for analyzing cardiac activity and cardiac events.

BACKGROUND

Monitoring devices for collecting biometric data are becoming increasingly common in diagnosing and treating medical conditions in patients. For example, mobile devices can be used to monitor cardiac data in a patient. This cardiac monitoring can empower physicians with valuable information regarding the occurrence and regularity of a variety of heart conditions and irregularities in patients. Cardiac monitoring can be used, for example, to identify abnormal cardiac rhythms, so that critical alerts can be provided to patients, physicians, or other care providers and patients can be treated.

SUMMARY

In Example 1, a method includes receiving, by a first computing system, electrocardiogram (ECG) data and metadata associated with the ECG data. The metadata includes an initial cardiac event classification and an initial beat classification for beats occurring during a first event associated with the initial cardiac event classification. The method further includes displaying the ECG data in a user interface, receiving a command to change the initial cardiac event classification to a subsequent cardiac event classification, and automatically modifying the initial beat classifications to subsequent beat classifications based on the subsequent cardiac event classification.

In Example 2, the method of Example 1, wherein the initial cardiac event classification is an atrial fibrillation event, a normal sinus event, or a ventricular tachycardia event, wherein the subsequent cardiac event classification is a supraventricular event, wherein the subsequent beat classifications are supraventricular beats.

In Example 3, the method of Example 1, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

In Example 4, the method of Example 1, wherein the initial cardiac event classification is a ventricular tachycardia event or a supraventricular event, wherein the subsequent cardiac event classification is a normal sinus event, wherein the subsequent beat classifications are normal beats.

In Example 5, the method of Example 1, wherein the initial cardiac event classification is a ventricular tachycardia event or a supraventricular event, wherein the subsequent cardiac event classification is an atrial fibrillation event, wherein the subsequent beat classifications are normal beats.

In Example 6, the method of any of the preceding Examples, wherein the initial beat classifications include a first beat type and a second beat type, wherein the automatically modifying the initial beat classifications to the subsequent beat classifications includes modifying only the first beat type.

In Example 7, the method of any of the preceding Examples, further including displaying, in the UI, the initial beat classifications and the initial cardiac event classification and, after the automatically modifying step, displaying the subsequent beat classifications and the subsequent cardiac event classification.

In Example 8, the method of any of the preceding Examples, wherein the initial beat classifications and the initial cardiac event classification are determined by a deep learning neural network operated by a server, wherein the subsequent beat classifications are determined by the first computing system.

In Example 9, the method of Example 8, wherein the subsequent beat classifications are determined by executing computer code by a web browser operating on the first computing system.

In Example 10, the method of Example 8, further including receiving, by the first computing system, the computer code in a data package that also includes the ECG data and the metadata.

In Example 11, the method of any of the preceding Examples, wherein the command is generated in response to receiving input, via the UI, from a user.

In Example 12, the method of any of the preceding Examples, further including receiving, by the first computing system, a second set of ECG data and a second set of metadata associated with the second set of ECG data. The second set of metadata includes a first cardiac event classification and a first beat classification for each beat occurring during a second event associated with the first cardiac event classification. The method further includes receiving a first command to change the first cardiac event classification to a second cardiac event classification and maintaining the first beat classifications to second beat classifications based on the second cardiac event classification.

In Example 13, a computer program product including instructions to cause one or more processors to carry out the steps of the method of Examples 1-12.

In Example 14, a computer-readable medium having stored thereon the computer program product of Example 13.

In Example 15, a computer including the computer-readable medium of Example 14.

In Example 16, a system includes a remote computing system with a UI, a first processor, and a first computer-readable medium having a first set of computer-executable instructions embodied thereon. The first set of instructions configured to be executed by the first processor to cause the first processor to: display the ECG data in the UI after receiving ECG data and metadata. The metadata including an initial cardiac event classification and an initial beat classification for beats occurring during a first event associated with the initial cardiac event classification. The first set of instructions are further configured to receive a command to change the initial cardiac event classification to a subsequent cardiac event classification and automatically modify the initial beat classifications to subsequent beat classifications based on the subsequent cardiac event classification.

In Example 17, the system of Example 16, wherein the command is generated in response to receiving input, via the UI, from a user.

In Example 18, the system of Example 16, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

In Example 19, the system of Example 16, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

In Example 20, the system of Example 16, wherein the initial cardiac event classification is a ventricular tachycardia event or a supraventricular event, wherein the subsequent cardiac event classification is a normal sinus event, wherein the subsequent beat classifications are normal beats.

In Example 21, the system of Example 16, wherein the initial cardiac event classification is a ventricular tachycardia event or a supraventricular event, wherein the subsequent cardiac event classification is an atrial fibrillation event, wherein the subsequent beat classifications are normal beats.

In Example 22, the system of Example 16, wherein the initial beat classifications include a first beat type and a second beat type, wherein the automatically modifying the initial beat classifications to the subsequent beat classifications includes modifying only the first beat type.

In Example 23, the system of Example 16, wherein the first set of instructions are configured to be executed by the first processor to cause the first processor to: display, in the UI, the initial beat classifications and the initial cardiac event classification and, after the automatically modifying step, display the subsequent beat classifications and the subsequent cardiac event classification.

In Example 24, the system of Example 16, wherein the first set of instructions are configured to be executed via a web browser at the remote computing system.

In Example 25, the system of Example 16, further including a server with a database, a second processor, and a second computer-readable medium having a second set of computer-executable instructions embodied thereon. The second set of instructions are configured to be executed by the second processor to cause the second processor to: determine, using a machine learning model operated by the server and based on ECG data, the initial cardiac event classification and the initial beat classifications. The instructions are further configured to cause the second processor to: store the initial cardiac event classification and initial beat classifications in the database; transmit, to the remote computing system, strips of the initial ECG data, the initial cardiac event classification, the initial beat classifications, and the first set of instructions; receive, from the remote computing system, the subsequent cardiac event classification and the subsequent beat classifications; and replace, in the database, the initial cardiac event classification with the subsequent cardiac event classification and the initial beat classifications with the subsequent beat classifications.

In Example 26, the system of Example 25, wherein the first set of instructions are executed by a web browser at the remote computing system.

In Example 27, a method includes receiving, by a first computing system, ECG data and metadata associated with the ECG data. The metadata includes an initial cardiac event classification and an initial beat classification for beats occurring during a first event associated with the initial cardiac event classification. The method further includes displaying the ECG data in a UI, receiving a command to change the initial cardiac event classification to a subsequent cardiac event classification, and automatically modifying the initial beat classifications to subsequent beat classifications based on the subsequent cardiac event classification.

In Example 28, the method of Example 27, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

In Example 29, the method of Example 27, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

In Example 30, the method of Example 27, wherein the initial cardiac event classification is a ventricular tachycardia event or a supraventricular event, wherein the subsequent cardiac event classification is a normal sinus event, wherein the subsequent beat classifications are normal beats.

In Example 31, the method of Example 27, wherein the initial cardiac event classification is a ventricular tachycardia event or a supraventricular event, wherein the subsequent cardiac event classification is an atrial fibrillation event, wherein the subsequent beat classifications are normal beats.

In Example 32, the method of Example 27, wherein the initial beat classifications include a first beat type and a second beat type, wherein the automatically modifying the initial beat classifications to the subsequent beat classifications comprises modifying only the first beat type.

In Example 33, the method of Example 27, wherein the subsequent beat classifications are determined by executing computer code by a web browser operating on the first computing system.

In Example 34, a method includes determining—using a machine learning model operated by a server and based on ECG data—an initial cardiac event classification and initial beat classifications for beats occurring during an event. The method further includes storing the initial cardiac event classification and initial beat classifications in a database of the server. The method further includes transmitting—to a remote computing system—strips of the initial ECG data, the initial cardiac event classification, the initial beat classifications, and executable code. The method further includes receiving, from the remote computing system, a subsequent cardiac event classification and subsequent beat classifications and replacing, in the database, the initial cardiac event classification with the subsequent cardiac event classification and the initial beat classifications with the subsequent beat classifications.

In Example 35, the method of Example 34, further including training the machine learning model with the subsequent cardiac event classification and the subsequent beat classifications.

While multiple instances are disclosed, still other instances of the present disclosure will become apparent to those skilled in the art from the following detailed description, which shows and describes illustrative instances of the disclosure. Accordingly, the drawings and detailed description are to be regarded as illustrative in nature and not restrictive.

BRIEF DESCRIPTION OF THE DRAWINGS

FIG. 6 shows a flow diagram depicting an illustrative method for reclassifying cardiac events and beat classifications, in accordance with instances of the disclosure.

FIG. 7 shows a flow diagram depicting an illustrative method for hosting a SaaS platform and updating a hosted database in response to changes to metadata made remotely, in accordance with instances of the disclosure.

Figure 1:
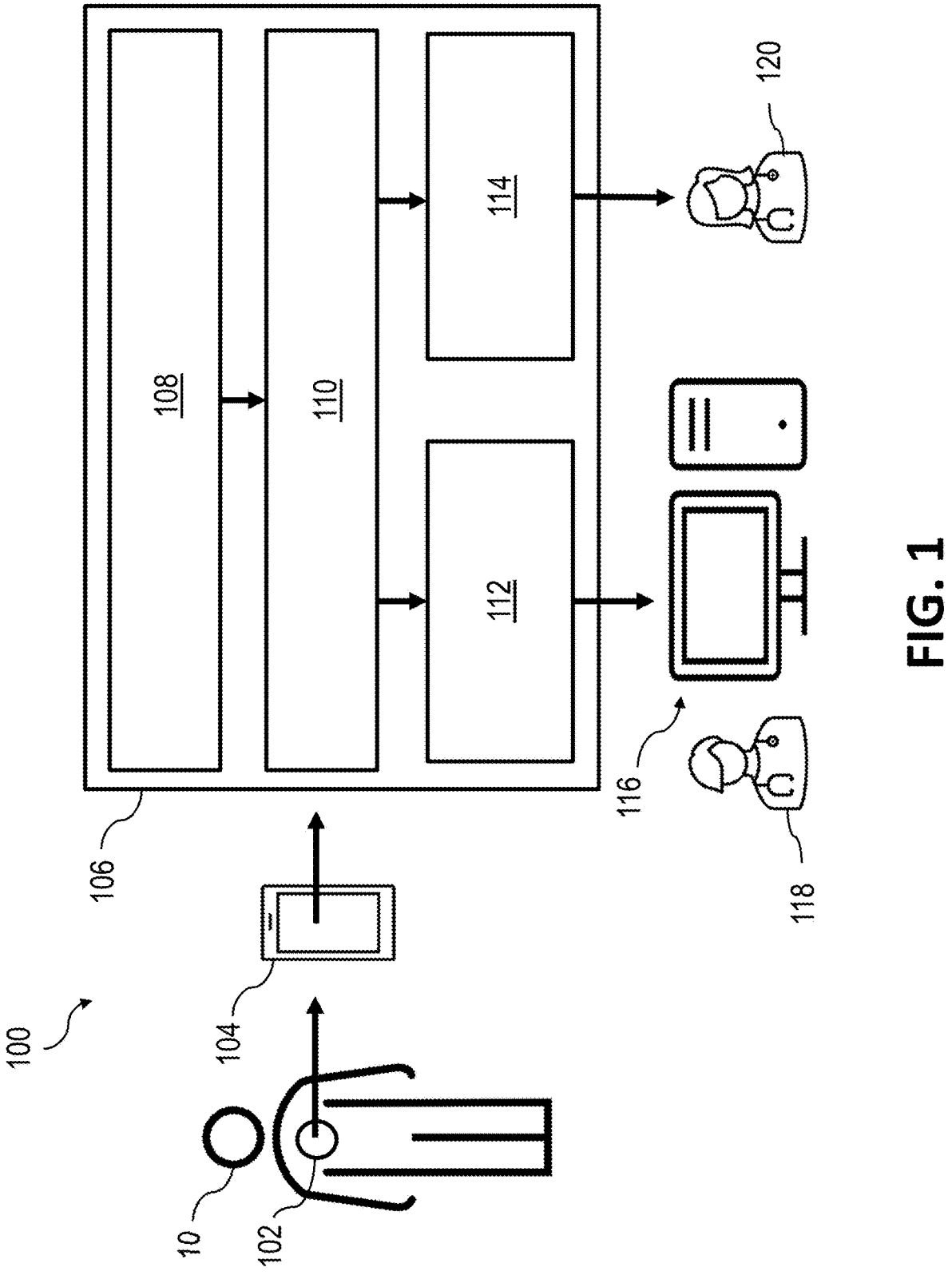
FIG. 1 shows a cardiac monitoring system, in accordance with certain instances of the present disclosure.

While the disclosed subject matter is amenable to various modifications and alternative forms, specific instances have been shown by way of example in the drawings and are described in detail below. The intention, however, is not to limit the disclosure to the particular instances described. On the contrary, the disclosure is intended to cover all modifications, equivalents, and alternatives falling within the scope of the disclosure as defined by the appended claims.

DETAILED DESCRIPTION

The present disclosure relates to devices, methods, and systems for facilitating analysis of cardiac activity and cardiac events (e.g., abnormal cardiac rhythms or other issues).

Electrocardiogram (ECG) data of a patient can be used to identify whether the patient has experienced a cardiac event and what type of cardiac event occurred. One input to determining the type of cardiac event includes the types (or classifications) of heartbeats experienced during the cardiac event. As such, an ECG analysis system may automatically determine that a certain type of cardiac event occurred based on—among other things—how the system classified the beats that occurred during the event. However, if the beats were initially misclassified, the determined type of cardiac event may also be misclassified. The cardiac event may then need to be reclassified. It follows, then, that the underlying beats may also need to be reclassified. Instances of the present disclosure are accordingly directed to systems, methods, and devices for facilitating reclassification of ECG data.

FIG. 1 illustrates a patient 10 and an example system 100. The system 100 includes a monitor 102 attached to the patient 10 to detect cardiac activity of the patient 10. The monitor 102 may produce electric signals that represent the cardiac activity in the patient 10. For example, the monitor 102 may detect the patient's heart beating (e.g., using infrared sensors, electrodes) and convert the detected heartbeat into electric signals representing ECG data. The monitor 102 communicates the ECG data to a mobile device 104 (e.g., a mobile phone).

The mobile device 104 may include a program (e.g., mobile phone application) that receives, processes, and analyzes the ECG data. For example, the program may analyze the ECG data and detect or flag cardiac events (e.g., periods of irregular cardiac activity) contained within the ECG data. As noted above, because ECG data may be getting continuously generated, the amount of ECG data can be overwhelming to store and process locally on the mobile device 104. As such, the mobile device 104 can periodically transmit chunks of the ECG data to another device or system, which can process, append together, and archive the chunks of the ECG data and metadata (e.g., time, duration, detected/flagged cardiac events) associated with the chunks of ECG data. In certain instances, the monitor 102 may be programmed to transmit the ECG data directly to the other device or system without utilizing the mobile device 104. Also, in certain instances, the monitor 102 and/or the mobile device 104 includes a button or touch-screen icon that allows the patient 10 to initiate an event. Such an indication can be recorded and communicated to the other device or system. In other instances involving multi-day studies, the ECG data and associated metadata are transmitted in larger chunks.

Cardiac Event Server

In the example shown in FIG. 1, the mobile device 104 transmits the ECG data (and associated metadata, if any) to a cardiac event server 106 (hereinafter "the server 106" for brevity). The server 106 includes multiple platforms, layers, or modules that work together to process and analyze the ECG data such that cardiac events can be detected, filtered, prioritized, and ultimately reported to a patient's physician for analysis and treatment. In the example of FIG. 1, the server 106 includes one or more machine learning models 108 (e.g., types of deep neural networks), a cardiac event router 110, a report platform 112, and a notification platform 114. Although only one server 106 is shown in FIG. 1, the server 106 can include multiple separate physical servers, and the various platforms/modules/layers can be distributed among the multiple servers. Each of the platforms/modules/layers can represent separate programs, applications, and/or blocks of code where the output of one of the platforms/modules/layers is an input to another of the platforms/modules/layers. Each platform/module/layer can use application programming interfaces to communicate between or among the other platforms/modules/layers as well as systems and devices external to the server 106.

The server 106 applies the machine learning model 108 to the ECG data to classify cardiac activity of the patient 10. For example, the machine learning model 108 may compare the ECG data to labeled ECG data to determine which labeled ECG data the ECG data most closely resembles. The labeled ECG data may identify a particular cardiac event, including but not limited to ventricular tachycardia, bradycardia, atrial fibrillation, pause, normal sinus rhythm, or artifact/noise. Further, the labeled ECG data may identify beat classifications such as normal, ventricular, and supraventricular.

In certain embodiments, the machine learning model 108 includes two paths, where the first path is a deep convolutional neural network and the second path is a deep fully-connected neural network. The deep convolutional neural network receives one or more sets of beats (e.g., beat trains with 3-10 beats) which are processed through a series of layers in the deep convolutional neural network. The series of layers can include a convolution layer to perform convolution on time series data in the beat trains, a batch normalization layer to normalize the output from the convolution layer (e.g., centering the results around an origin), and a non-linear activation function layer to receive the normalized values from the batch normalization layer. The beat trains then pass through a repeating set of layers such as another convolution layer, a batch normalization layer, a non-linear activation function layer. This set of layers can be repeated multiple times.

The deep fully connected neural network receives RR-interval data (e.g., time intervals between adjacent beats) and processes the RR-interval data through a series of layers: a fully connected layer, a non-linear activation function layer, another fully connected layer, another non-linear activation function layer, and a regularization layer. The output from the two paths is then provided to the fully connected layer. The resulting values are passed through a fully connected layer and a softmax layer to produce probability distributions for the classes of beats.

If the machine learning model 108 determines that the ECG data most closely resembles a labeled ECG data associated with a cardiac event, then the machine learning model 108 may determine that the patient 10 has experienced that cardiac event. Additionally, the machine learning model 108 may measure or determine certain characteristics of the cardiac activity of the patient 10 based on the ECG data. For example, the machine learning model 108 may determine a heart rate, a duration, or a beat count of the patient 10 during the cardiac event based on the ECG data. The server 106 stores the cardiac event (and associated metadata such as information like beat classification, heart rate, duration, beat count, etc.) in a database for storage. Subsequently, the server 106 may retrieve the cardiac event and associated information from the database.

In certain instances, the mobile device 104 (or monitor 102) may initially classify a cardiac event based on the ECG data. The server 106 may then re-classify or confirm the cardiac event using the machine learning model 108. Doing so allows for a more computationally-expensive analysis of the ECG data to be performed using the computing resources of the server 106, rather than the limited resources of the mobile device 104.

In certain instances, once the ECG data is processed by the machine learning model 108, the ECG data and metadata is made available for the report platform 112. As will be described in more detail below, the report platform 112 can be accessed by a remote computer 116 (e.g., client device such as a laptop, mobile phone, desktop computer, and the like) by a user at a clinic or lab 118.

In other instances, the cardiac event router 110 is used to determine what platform further processes the ECG data based on the classification associated with the cardiac event. For example, if the identified cardiac event is severe, the cardiac event router 110 can flag or send the ECG data, etc., to the notification platform 114. The notification platform 114 can be programmed to send notifications (along with relevant ECG data and associated metadata) immediately to the patient's physician/care group remote computer and/or to the patient 10 (e.g., to their computer system, e-mail, mobile phone application).

Report Platform

Figure 2:
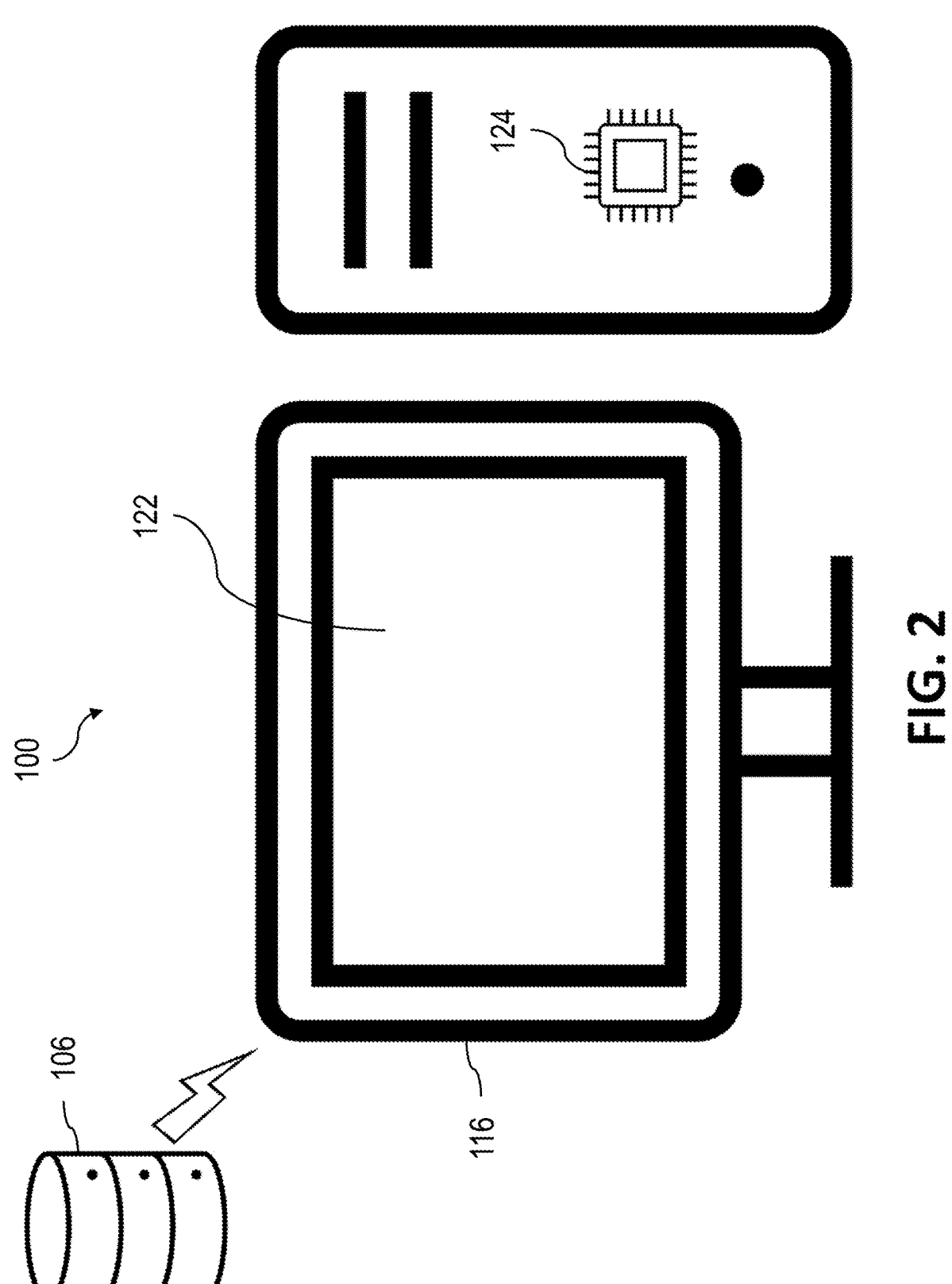
FIG. 2 shows a server, remote computer, and user interface, in accordance with certain instances of the present disclosure.

FIG. 2 shows the server 106 communicatively coupled (e.g., via a network) to the remote computer 116. In the example of FIG. 2, the remote computer 116 includes a monitor showing a user interface 122 (hereinafter "the UI 122" for brevity) that displays features of the report platform 112 hosted by the server 106. The UI 122 includes multiple pages or screens for tracking and facilitating analysis of patient ECG data.

In certain instances, the report platform 112 is a software-as-a-service (SaaS) platform hosted by the server 106. To access the report platform 112, a user (e.g., a technician) interacts with the UI 122 to log into the report platform 112 via a web browser such that the user can use and interact with the report platform 112. When the user at the clinic or lab 118 is ready to analyze ECG data of a patient, the user can select a patient's profile through the UI 122.

The server 106 (e.g., via programming associated with the report platform 112) can start a process for sending data to the remote computer 116. This data includes the ECG data and metadata associated with the ECG data. As noted above, once the ECG data from the monitored patients has been collected, the machine learning model 108 may determine certain characteristics of the cardiac activity of the patient 10 based on the ECG data, including estimating that a cardiac event has occurred and associating or generating metadata for the determined events. The metadata can include information about the patient 10, a heart rate of the patient 10 during the cardiac event, a duration of the cardiac event, a beat count of the cardiac event, a confidence level of the machine learning model's identification of the cardiac event, and/or a beat classification (e.g., normal, ventricular, supraventricular, unclassified).

In certain instances, the machine learning model 108 assigns each beat with a beat classification and also assigns, for certain groups and patterns of beats, a cardiac event type (e.g., atrial fibrillation, ventricular tachycardia, flutter). To distinguish among the beats, each individual beat can therefore be assigned a unique identifier (e.g., a unique number).

Accessing, processing, and displaying one or more days' worth of ECG data and metadata can consume a large amount of computing resources, network bandwidth resources, and human resources. To help alleviate burdens on these resources, the server 106 (e.g., via the report platform 112) can selectively transmit packages of ECG data and metadata to the remote computer 116.

The initial packages of data can include: (1) short strips of ECG data surrounding detected cardiac events, (2) metadata associated with the strips, and (3) executable code (e.g., JavaScript code). In certain instances, only the ECG data associated with highest priority cardiac events are initially transferred. After the initial packages of data are transmitted from the server to the remote computer 116, additional packages of data can be transmitted in response to selections made by the user in the UI 122.

Report Build Page

Figure 3:
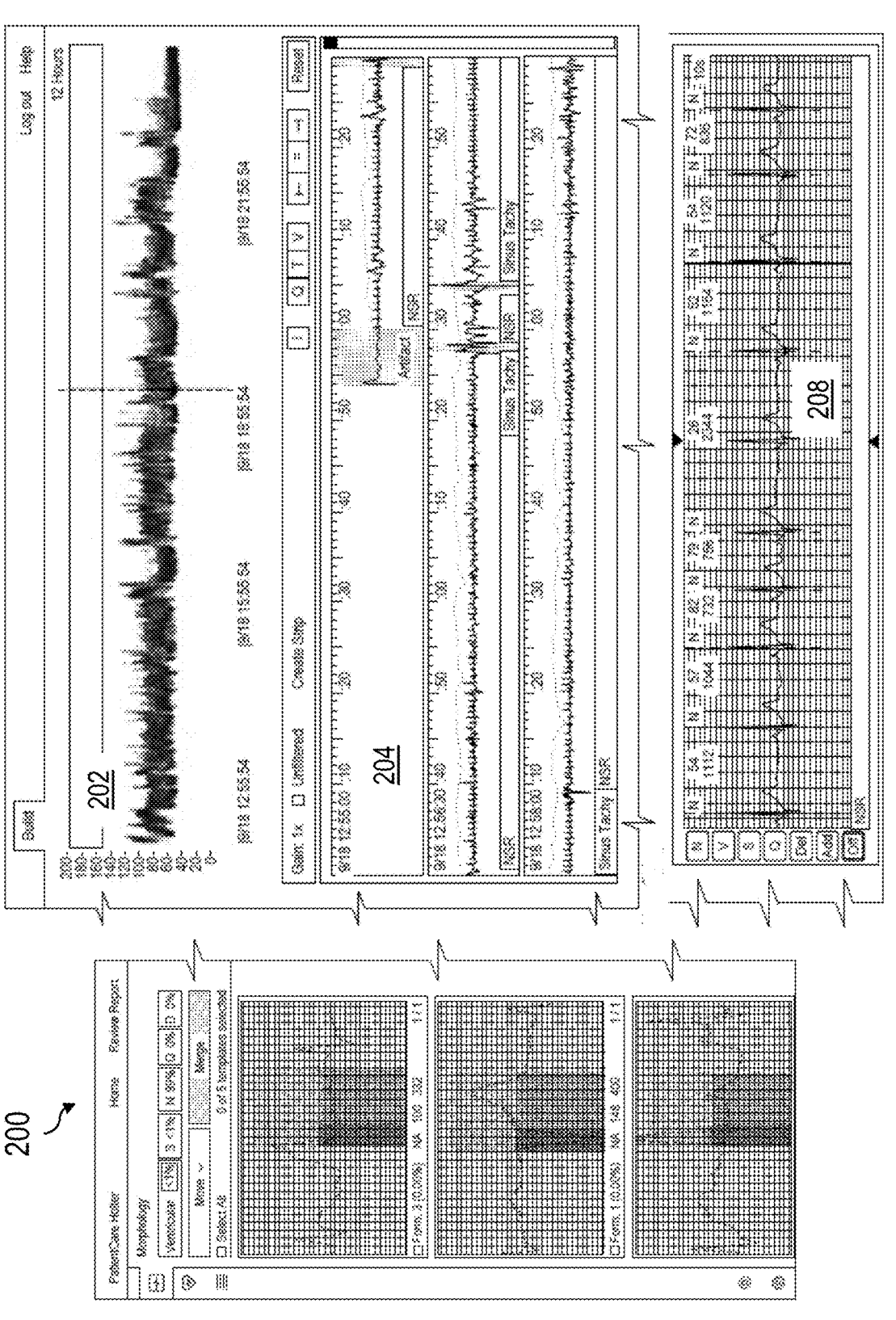
FIGS. 3-5 show various views of a report build page, in accordance with certain instances of the present disclosure.
Figure 4:
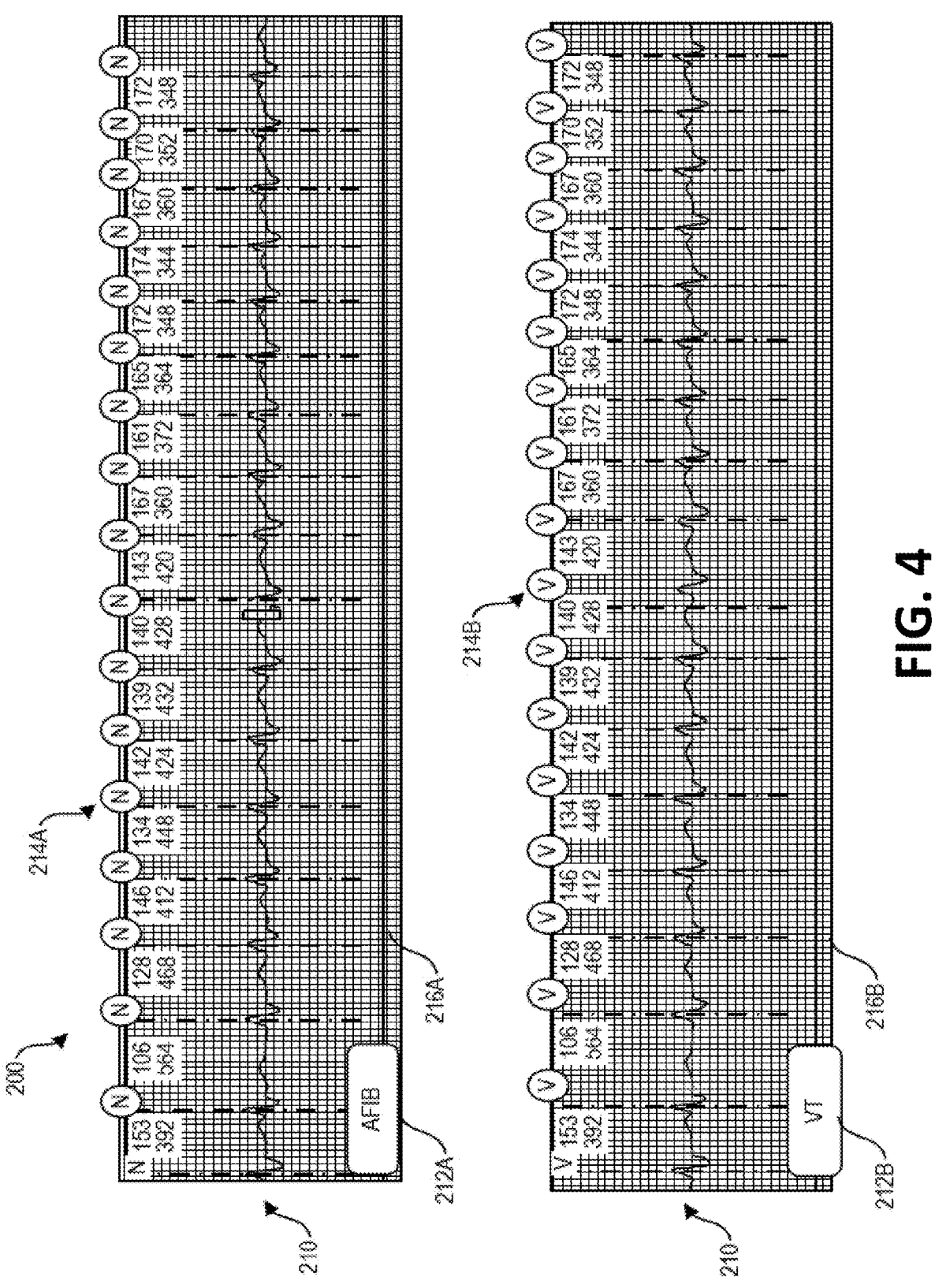
Figure 5:
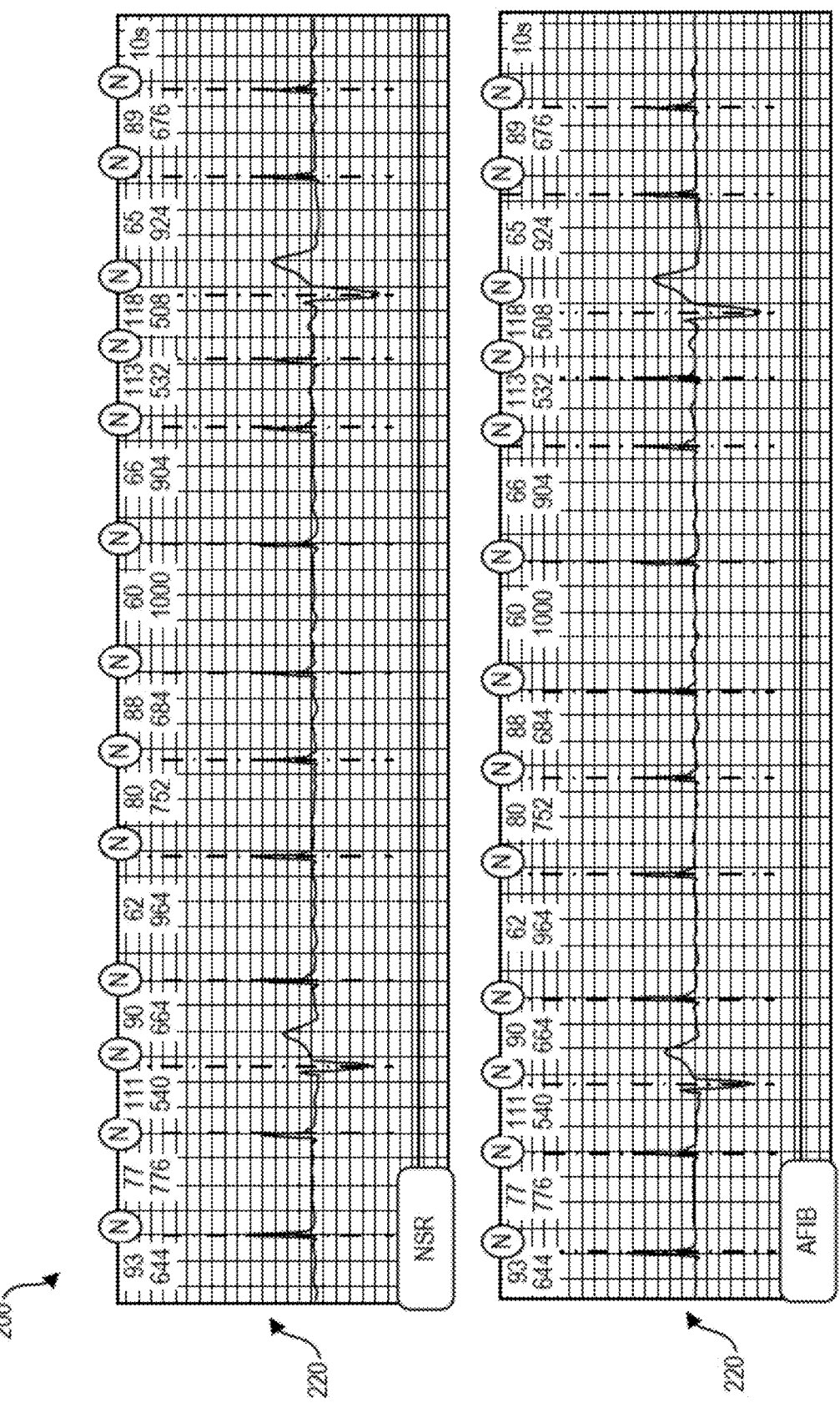

With these initial packages of data, the user has access (via the remote computer 116 and the UI 122) to a report build page 200 shown in FIGS. 3-5. The report build page 200 facilitates analysis of cardiac events and metadata associated with the cardiac events. The pages are generated at the remote computer 116 based on the packages of data and they are selectively displayed via the UI 122. As will be described in more detail below, as the user interacts with the report build page 200, the metadata is updated in real time at the remote computer 116.

FIG. 3 shows a screenshot of the report build page 200. The report build page 200 is used by a user to review and analyze a patient's ECG data and metadata. The report build page 200 includes multiple windows for displaying data, plots, icons, links, markers, indicators, and the like.

Window 202 displays a heart rate plot of multiple days' worth of ECG data. This window 202 provides an initial visual insight into which periods of time appear to contain abnormal heart rate activity. In the example of FIG. 3, the window 202 displays four days of ECG data, although shorter or longer time periods could be displayed by default or changed by the user.

Window 204 allows the user to view a shorter plot of ECG data. For example, the window 204 may display ECG data associated with a detected cardiac event along with ECG data preceding and following the detected event. This window 204 provides visual insight into the onset of a detected event and whether the detected event is perhaps an artifact, follow-on event, etc. As the user scrolls through the window 204, the window 202 can display an indicator (e.g., a vertical line) showing the location of the ECG data of window 204 within the heart rate plot of window 202.

Window 208 shows a plot of ECG data (e.g., approximately 10 beats) that is shorter than the plots of windows 202 and 204. Window 208 displays a closer-up view of a portion of the ECG data of windows 202 and 204. The user can use window 204 to select which shorter set of ECG data is displayed in the window 208. Each of the windows 202, 204, and 208 can include markers, indicators, icons, etc., to visually note the location of detected cardiac events within the strips of ECG data.

Event and Beat Reclassification

As noted above, the machine learning model 108 can be programmed to automatically identify and classify cardiac events and types of beats. These initial classifications are sent from the server 106 to the remote computer 116 for analysis. If during the analysis a user determines that the initial classification should be updated, the report build page 200 allows the user to reclassify the cardiac events and beats via the UI 122 at the remove computer 116. As described in more detail below, a reclassification made in the report build page 200 to a cardiac event can lead to automatically reclassifying beats that occurred during the event—instead of requiring a user to manually analyze and reclassify each of the beats. This automatic reclassification of beats saves time analyzing ECG data and generating summary reports while also increasing accuracy of the overall ECG studies.

FIG. 4 shows a portion of the report build page 200. The top part of FIG. 4 shows a strip 210 of ECG data containing a cardiac event with its initial event and beat classifications, and the bottom part of FIG. 4 shows the strip 210 of ECG data with modified (or subsequent) event and beat classifications.

In the top half of FIG. 4, the strip 210 of ECG data displays the initial classification of the cardiac event and the initial beat classifications in respective icons 212A and 214A. The initial classifications are based on the metadata generated by the machine learning model 108 at the server 106 and received by the remote computer 116.

In the example of FIG. 4, the initial cardiac event classification is shown in the icon 212A as an atrial fibrillation event. The length of the initial cardiac event is visually shown by a band 216A that extends horizontally along the strip 210 of the ECG data between the onset of the event and the end of the event.

Each identified beat is given its own classification, which is shown with icons 214A adjacent to each beat. In the example of FIG. 4, the beats are classified as being normal beats, which are indicated by the letter "N" in the icons 214A. The strip 210 of ECG data also displays the length of RR intervals for respective pairs of identified beats.

When analyzing the ECG data, the user viewing the strip 210 of the ECG data may determine that the initial cardiac event classification should be changed to a different cardiac event classification. Using the icon 212A (or buttons on the report build page 200), the user can modify the initial cardiac event classification. In the example of FIG. 4, the user can change the cardiac event classification from an atrial fibrillation event to a ventricular tachycardia event. For example, the user can select a feature on the UI 122 (e.g., the icon 212A or various buttons), which generates a command to change the initial classification from an atrial fibrillation event to a subsequent classification of a ventricular tachycardia event. The metadata can then be updated to reflect this reclassification of the cardiac event.

In addition to reclassifying the cardiac event using the UI 122, the beat classifications can be updated automatically.

As noted above, certain types of beats are typically associated with certain types of cardiac events. As one example, supraventricular tachycardia events are typically associated with beats classified as supraventricular beats. As such, when a cardiac event is subsequently classified as a supraventricular tachycardia event, each of the beats occurring during that event can be reclassified to be supraventricular beats. As another example, atrial fibrillation events are typically associated with beats classified as normal beats. As such, when a cardiac event is subsequently classified as an atrial fibrillation event, each of the beats occurring during that event can be reclassified to be normal beats. Below is a table that outlines examples of how beats will be automatically classified based on the subsequent cardiac event classification:

TABLE 1

| | Subsequent classifications | | | |
|---|---|---|---|---|
| | AFib | NSR | VT | SVT |
| AFib | | Z | V | S |
| NSR | Z | | V | S |
| VT | N | N | | S |
| SVT | N | N | V | |

The first column represents the initial cardiac event classifications, and the upper row represents the subsequent cardiac event classifications. In Table 1, Afib represents an atrial fibrillation event, NSR represents a normal sinus event, VT represents a ventricular tachycardia event, and SVT represents a supraventricular tachycardia event.

The single letters in the cells represent the subsequent beat classifications. In Table 1, "S" represents supraventricular beats, "V" represents ventricular beats, "N" represents normal beats, and "Z" represents no change.

As noted by the cells with a "Z", certain changes in cardiac event classifications do not affect the beat classifications. In such situations, the underlying beat classifications are compatible with the subsequent cardiac event classification, and therefore the initial beat classifications are maintained despite a change in the cardiac event classification.

Further, in certain instances, not all beats within a cardiac event may be initially classified the same. In such situations, only a subset of beats may be reclassified in response to modifying the initial cardiac event classification.

Referring back to the example of FIG. 4 and applying Table 1, it can be seen that changing the cardiac event classification from an atrial fibrillation event to a ventricular tachycardia event causes the beats occurring within the event to change to ventricular beat classifications.

FIG. 5 provides another example. FIG. 5 shows a portion of the report build page 200. The top part of FIG. 5 shows a strip 220 of ECG data containing a cardiac event with its initial event and beat classifications, and the bottom part of FIG. 5 shows the strip 220 of ECG data with modified (or subsequent) event and beat classifications.

In the top half of FIG. 5, the strip 220 of ECG data displays the initial classification of the cardiac event and the initial beat classifications in respective icons. In the example of FIG. 5, the initial cardiac event classification is shown as a normal sinus event. The beats are classified as being normal beats.

In the example of FIG. 5, the user can change the cardiac event classification from a normal sinus event to an atrial fibrillation event. Applying Table 1, it can be seen that changing the cardiac event classification from a normal sinus event to an atrial fibrillation event causes the beats occurring within the event to remain as normal beats. This is because both types of cardiac events are likely to include normal beats, as opposed to other types of beats. As such, for this specific example, the beat classifications are not modified in response to the change in the cardiac event classification.

To save processing and network resources and to allow these changes to metadata to occur in real-time, the calculations and changes to the cardiac event classifications and the automatic updates to the beat classifications can be carried out locally on the remote computer 116—as opposed to sending data back and forth between the server 106 and the remote computer 116. For example, the reclassifications can be carried out using cache memory 124 (shown in FIG. 1) and processing capabilities (e.g., one or more microprocessors) of the remote computer 116. To enable local processing and updating, the report platform 112 can send the remote computer 116 code to execute locally. This code uses (or operates on) the outputs of the machine learning model 108 such as the beat classifications and rhythm classifications (as opposed to the underlying or raw ECG data), which reduces the computational resources needed to process the changes made by user locally at the remote computer 116. In certain embodiments, this code is executed by an internet browser operating on the remote computer 116.

In certain instances, once the report is built and complete, the remote computer 116 can send any changes to the metadata (e.g., the subsequent beat classifications and the subsequent rhythm classifications) to the server 106 and its database. The server 106 can then replace the metadata initially created by the machine learning model (and saved to the database) with the metadata generated by the remote computer while the user was reviewing and editing the metadata. As such, if the ECG and metadata need to be accessed again, the server's database has the most recent version of the metadata. Further, the machine learning model 108 may be further trained on the metadata generated by the user at the remote computer.

METHODS

FIG. 6 shows a block diagram of a method 400 for reclassifying beats. The method 400 includes receiving ECG data and metadata associated with the ECG data (block 402 in FIG. 6). The metadata includes an initial cardiac event classification and an initial beat classification for each beat occurring during a first event associated with the initial cardiac event classification. The method 400 further includes displaying the ECG data in a user interface (UI) (block 404 in FIG. 6). The method 400 further includes receiving a command to change the initial cardiac event classification to a subsequent cardiac event classification (block 406 in FIG. 6). The method 400 further includes automatically modifying the initial beat classifications to subsequent beat classifications based on the subsequent cardiac event classification (block 408 in FIG. 6).

FIG. 7 shows a block diagram of a method 500 for hosting a SaaS platform and updating a hosted database in response to changes to metadata made remotely. The method 500 includes identifying, using a machine learning model operated by a server, cardiac events within the ECG data and determining initial cardiac event classifications and initial beat classifications (block 502 in FIG. 7). The method 500 further includes transmitting—to a remote computing system—strips of the ECG data, the initial cardiac event classifications, the initial beat classifications, and executable code (block 504 in FIG. 7). The method further includes replacing, in the database, the initial cardiac event classifications and the initial beat classifications generated by the remote computing system (block 506 in FIG. 7).

Computing Devices and Systems

Figure 8:
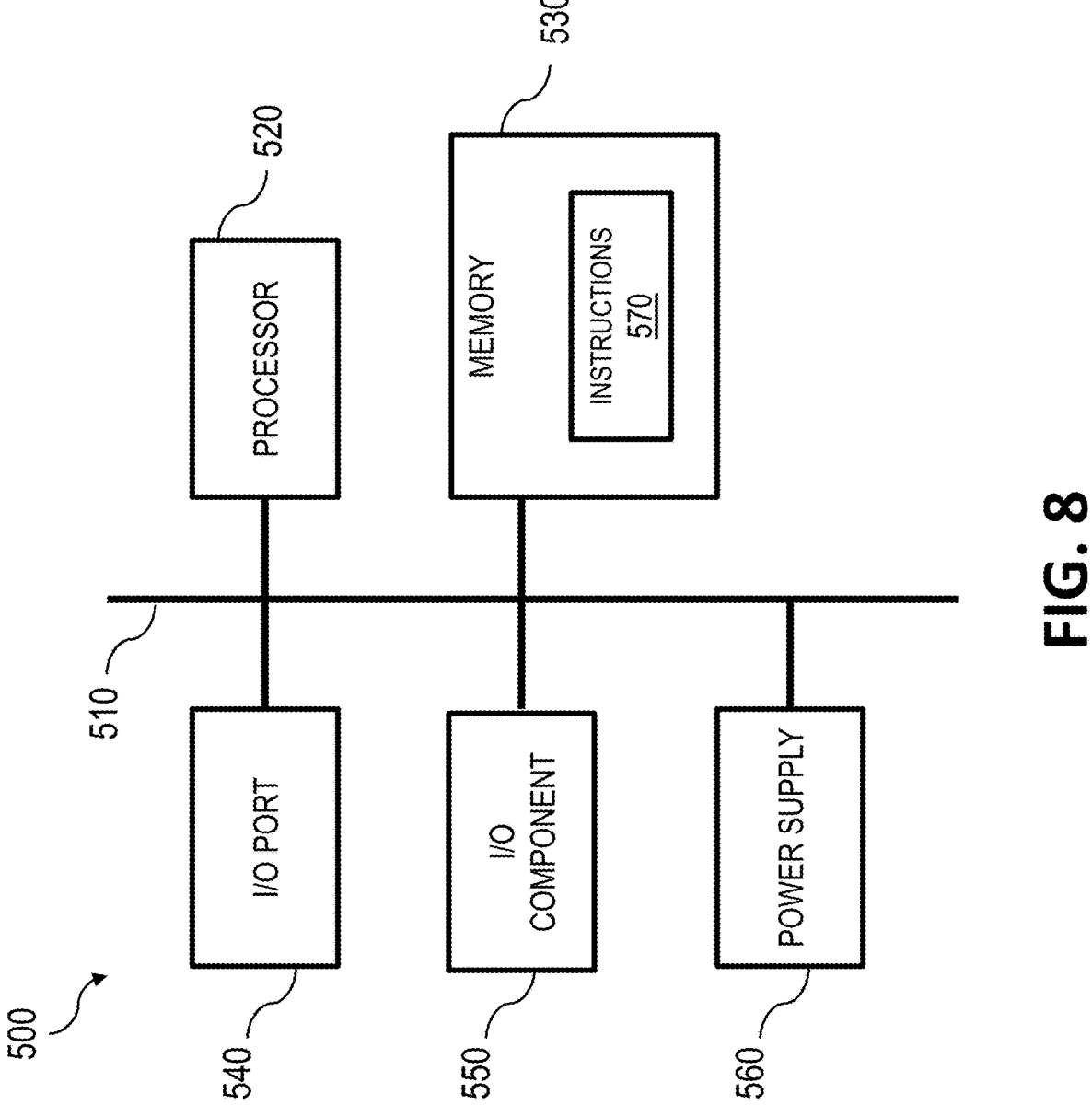
FIG. 8 is a block diagram depicting an illustrative computing device, in accordance with instances of the disclosure.

FIG. 8 is a block diagram depicting an illustrative computing device 500, in accordance with instances of the disclosure. The computing device 500 may include any type of computing device suitable for implementing aspects of instances of the disclosed subject matter. Examples of computing devices include specialized computing devices or general-purpose computing devices such as workstations, servers, laptops, desktops, tablet computers, hand-held devices, smartphones, general-purpose graphics processing units (GPGPUs), and the like. Each of the various components shown and described in the Figures can contain their own dedicated set of computing device components shown in FIG. 5 and described below. For example, the mobile device 104, the server 106, and the remote computer 116 can each include their own set of components shown in FIG. 8 and described below.

In instances, the computing device 500 includes a bus 510 that, directly and/or indirectly, couples one or more of the following devices: a processor 520, a memory 530, an input/output (I/O) port 540, an I/O component 550, and a power supply 560. Any number of additional components, different components, and/or combinations of components may also be included in the computing device 500.

The bus 510 represents what may be one or more busses (such as, for example, an address bus, data bus, or combination thereof). Similarly, in instances, the computing device 500 may include a number of processors 520, a number of memory components 530, a number of I/O ports 540, a number of I/O components 550, and/or a number of power supplies 560. Additionally, any number of these components, or combinations thereof, may be distributed and/or duplicated across a number of computing devices.

In instances, the memory 530 includes computer-readable media in the form of volatile and/or nonvolatile memory and may be removable, nonremovable, or a combination thereof. Media examples include random access memory (RAM); read only memory (ROM); electronically erasable programmable read only memory (EEPROM); flash memory; optical or holographic media; magnetic cassettes, magnetic tape, magnetic disk storage or other magnetic storage devices; data transmissions; and/or any other medium that can be used to store information and can be accessed by a computing device. In instances, the memory 530 stores computer-executable instructions 570 for causing the processor 520 to implement aspects of instances of components discussed herein and/or to perform aspects of instances of methods and procedures discussed herein. The memory 530 can comprise a non-transitory computer readable medium storing the computer-executable instructions 570.

The computer-executable instructions 570 may include, for example, computer code, machine-useable instructions, and the like such as, for example, program components capable of being executed by one or more processors 520 (e.g., microprocessors) associated with the computing device 500. Program components may be programmed using any number of different programming environments, including various languages, development kits, frameworks, and/or or the like. Some or all of the functionality contemplated herein may also, or alternatively, be implemented in hardware and/or firmware.

According to instances, for example, the instructions 570 may be configured to be executed by the processor 520 and, upon execution, to cause the processor 520 to perform certain processes. In certain instances, the processor 520, memory 530, and instructions 570 are part of a controller such as an application specific integrated circuit (ASIC), field-programmable gate array (FPGA), and/or the like. Such devices can be used to carry out the functions and steps described herein.

The I/O component 550 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The devices and systems described herein can be communicatively coupled via a network, which may include a local area network (LAN), a wide area network (WAN), a cellular data network, via the internet using an internet service provider, and the like.

Aspects of the present disclosure are described with reference to flowchart illustrations and/or block diagrams of methods, devices, systems and computer program products. It will be understood that each block of the flowchart illustrations and/or block diagrams, and combinations of blocks in the flowchart illustrations and/or block diagrams, can be implemented by computer program instructions.

Various modifications and additions can be made to the exemplary instances discussed without departing from the scope of the disclosed subject matter. For example, while the instances described above refer to particular features, the scope of this disclosure also includes instances having different combinations of features and instances that do not include all of the described features. Accordingly, the scope of the disclosed subject matter is intended to embrace all such alternatives, modifications, and variations as fall within the scope of the claims, together with all equivalents thereof.

We claim:

1. A system comprising:
    a remote computing system comprising: a user interface (UI), a first processor, and a first computer-readable medium having a first set of computer-executable instructions embodied thereon, the first set of instructions configured to be executed to cause the remote computing system to:
        after receiving electrocardiogram (ECG) data, the first set of computer-executable instructions, and metadata including an initial cardiac event classification and an initial beat classification for each beat occurring during a first event associated with the initial cardiac event classification: display the ECG data in the UI;
        receive a command, via user input to the UI, to change the initial cardiac event classification to a subsequent cardiac event classification;
        modify the initial cardiac event classification of the first event to the subsequent cardiac event classification; and
        automatically modify the initial beat classifications to subsequent beat classifications based on the subsequent cardiac event classification selected via the UI.

2. The system of claim 1, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

3. The system of claim 1, wherein the initial cardiac event classification is a ventricular tachycardia event or a supraventricular event, wherein the subsequent cardiac event classification is a normal sinus event, wherein the subsequent beat classifications are normal beats.

4. The system of claim 1, wherein the initial cardiac event classification is a ventricular tachycardia event or a supraventricular event, wherein the subsequent cardiac event classification is an atrial fibrillation event, wherein the subsequent beat classifications are normal beats.

5. The system of claim 1, wherein the initial beat classifications include a first beat type and a second beat type, wherein the automatically modifying the initial beat classifications to the subsequent beat classifications comprises modifying only the first beat type.

6. The system of claim 1, wherein the first set of instructions are configured to be executed by the first processor to cause the first processor to:
    display, in the UI, the initial beat classifications and the initial cardiac event classification; and
    after the automatically modifying step, display the subsequent beat classifications and the subsequent cardiac event classification.

7. The system of claim 1, wherein the first set of instructions are configured to be executed via a web browser at the remote computing system.

8. The system of claim 1, further comprising:
    a server comprising: a database, a second processor, and a second computer-readable medium having a second set of computer-executable instructions embodied thereon, the second set of instructions configured to be executed by the second processor to cause the second processor to:
        determine, using a machine learning model operated by the server and based on ECG data, the initial cardiac event classification and the initial beat classifications;
        store the initial cardiac event classification and initial beat classifications in the database;
        transmit, to the remote computing system, strips of the initial ECG data, the initial cardiac event classification, the initial beat classifications, and the first set of instructions;
        receive, from the remote computing system, the subsequent cardiac event classification and the subsequent beat classifications; and
        replace, in the database, the initial cardiac event classification with the subsequent cardiac event classification and the initial beat classifications with the subsequent beat classifications.

9. The system of claim 8, wherein the first set of instructions are executed by a web browser at the remote computing system.

10. The system of claim 1, wherein the automatically modify is carried out without using processing resources of a server.

11. A method comprising:
    receiving, by a first computing system, electrocardiogram (ECG) data and metadata associated with the ECG data, the metadata comprising an initial cardiac event classification and an initial beat classification for each separate beat occurring during a first event associated with the initial cardiac event classification;
    displaying the ECG data in a user interface (UI);

receiving, via the UI, a command to change the initial cardiac event classification to a subsequent cardiac event classification;

modifying the initial cardiac event classification of the first event to the subsequent cardiac event classification; and automatically modifying the initial beat classifications to subsequent beat classifications based on the subsequent cardiac event classification selected via the UI.

12. The method of claim 11, wherein the initial cardiac event classification is an atrial fibrillation event, a normal sinus event, or a supraventricular event, wherein the subsequent cardiac event classification is a ventricular tachycardia event, wherein the subsequent beat classifications are ventricular beats.

13. The method of claim 11, wherein the initial cardiac event classification is a ventricular tachycardia event or a supraventricular event, wherein the subsequent cardiac event classification is a normal sinus event, wherein the subsequent beat classifications are normal beats.

14. The method of claim 11, wherein the initial cardiac event classification is a ventricular tachycardia event or a supraventricular event, wherein the subsequent cardiac event classification is an atrial fibrillation event, wherein the subsequent beat classifications are normal beats.

15. The method of claim 11, wherein the initial beat classifications include a first beat type and a second beat type, wherein the automatically modifying the initial beat classifications to the subsequent beat classifications comprises modifying only the first beat type.

16. The method of claim 11, wherein the subsequent beat classifications are determined by executing computer code by a web browser operating on the first computing system.

17. The method of claim 11, further comprising: receiving, by the first computing system, executable computer code from a server, wherein the automatically modifying is carried out using the executable computer code using one or more microprocessors of the first computing system.

18. The method of claim 17, wherein the automatically modifying is carried out without using processing resources of the server.

* * * * *